United States Patent [19]

Bille et al.

[11] Patent Number: 4,881,808
[45] Date of Patent: Nov. 21, 1989

[54] IMAGING SYSTEM FOR SURGICAL LASERS

[75] Inventors: Josef F. Bille, Solana Beach; Stuart I. Brown, La Jolla, both of Calif.

[73] Assignee: Intelligent Surgical Lasers, La Jolla, Calif.

[21] Appl. No.: 154,966

[22] Filed: Feb. 10, 1988

[51] Int. Cl.$^4$ ............................................. A61B 3/10
[52] U.S. Cl. ..................................... 351/221; 351/246
[58] Field of Search ....................... 351/206, 221, 246; 128/303.1

[56] References Cited

U.S. PATENT DOCUMENTS

| | | | |
|---|---|---|---|
| 4,053,845 | 10/1977 | Gould | 330/4.3 |
| 4,161,436 | 7/1979 | Gould | 204/157.1 R |
| 4,503,854 | 3/1985 | Jako | 128/303.1 |
| 4,517,980 | 5/1985 | Tagnon | 128/395 |
| 4,561,436 | 12/1985 | Munnerlyn | 128/303.1 |
| 4,579,430 | 4/1986 | Bille | 351/206 |
| 4,598,311 | 7/1986 | Bellina | 358/93 |
| 4,601,288 | 7/1986 | Myers | 128/303.1 |
| 4,665,913 | 5/1987 | L'Esperance, Jr. | 128/303.1 |
| 4,669,466 | 6/1987 | L'Esperance | 128/303.1 |
| 4,704,583 | 11/1987 | Gould | 330/4.3 |
| 4,781,453 | 11/1988 | Kobayashi | 351/221 |

OTHER PUBLICATIONS

U.S. Patent Application No. 706,619, in the Name of Bille, Filed Oct. 22, 1987, "Apparatus for, and Method of, Examining Eyes".

"FM-Laser Operation of the Nd:YAG Laser," by Kuizenga et al., IEEE Journal of Quantum Electronics, Nov. 1970.

*Primary Examiner*—P. M. Dzierzynski
*Attorney, Agent, or Firm*—Nydegger & Harshman

[57] ABSTRACT

An ocular imaging system for use with a surgical laser device comprises a light source radiating a beam which is coaxially aligned with the surgical laser beam. An aperture is place in the path of the beams to limit the quantity of light that can pass along the path. A steering mechanism is provided to move the coaxially aligned beams across the surface of the eye, and a confocal optical arrangement is provided to establish one of the beams' focal points at the aperture and the other as desired by the operator. Means are provided to detect the intensity of light reflected through the aperture and signal when this intensity surpasses a threshold value that is indicative of a specular reflection from the interface between tissues having different indices of refraction.

17 Claims, 2 Drawing Sheets

IMAGING SYSTEM FOR SURGICAL LASERS

BACKGROUND OF THE INVENTION

This invention relates generally to optical imaging systems. More particularly, this invention relates to an imaging system which detects specular reflections from the interface between media having different indices of refraction. The present invention is particularly, but not exclusively, useful in ocular or ophthalmic surgery for identifying tissue boundaries or cavities within tissues.

DISCUSSION OF THE PRIOR ART

Advances in the various medical arts have now made surgical procedures possible which just a few years ago were only speculative. One important tool in this progress is the surgical laser. As is well known in the medical field, surgical lasers can be very efficaciously employed for certain purposes. This efficacy, however, is extremely dependent on the controllability of the laser and an exact identification of the tissue being operated on.

Not surprisingly, whenever a laser is used to perform very intricate and precise surgical procedures, there is a need for monitoring the subject tissue. This is particularly so in ophthalmic surgery where sensitive and delicate tissue is involved. Accordingly, several devices have been proposed which are capable of imaging portions of the tye for the purpose of observing the surgical procedure. Exemplary of such devices is U.S. Pat. No. 4,598,311 to Bille which discloses optical means for viewing an operative field. This device does not, however, precisely identify the location of a tissue boundary. Instead, its information relates to surface topography rather than the establishment of a reference datum. Imaging systems have also been proposed which are useful for diagnostic purposes. Exemplary of such a system is the disclosure In re application of Bille, application Ser. No. 706,619 filed on Oct. 11, 1987 for an invention entitled "Apparatus for, and Method of, Examining Eyes." Unlike the present invention where the desired information is primarily the geometric relationship between tissue masses, a diagnostic image is more concerned with detecting aberrations or abnormalities of the tissue. While these examples evidence means by which information concerning certain physical characteristics of the tissue within the field of view can be obtained, additional information concerning the size, shape and geometrical relationships of a tissue mass may be of equal or even more value in certain procedures.

The present invention recognizes there is a need in certain surgical procedures to precisely determine the boundary of the tissue being operated on. Specifically, corneal surgery represents such a requirement. Because of the layered structure of the cornea, the present invention recognizes that the ability to accurately identify the boundary between the cornea and the aqueous humor can be extremely helpful. With such information, operations at the interface between the cornea and the aqueous humor can be performed. Equally important, by using this interface as a reference datum, operations within the cornea can be performed without compromising the interface. Additionally, the present invention recognizes that the ability to monitor affected tissue within the cornea during the actual cutting procedure can be very helpful when creating internal ablations in the stroma. Further, the present invention recognizes that such identification and monitoring can be accomplished by detecting intensity variations in the light that is specularly reflected from the interface between media having different indices of refraction.

In light of the above, it is an object of the present invention to provide an imaging system for use in conjunction with a surgical laser that will accurately identify the interface between materials or media having different indices of refraction. Another object of the present invention is to provide an imaging system which will give indications of the location of internal ablations in the cornea either during or after the time the internal ablation is being created. Still another object of the present invention is to provide a system which will identify a reference datum from which an ophthalmic surgical laser operation can be performed. Yet another object of this invention is to provide an imaging system which is cost effective, relatively inexpensive to manufacture and easy to use.

SUMMARY OF THE INVENTION

A preferred embodiment of the novel imaging system of the present invention includes a light source which directs a beam of light toward the eye. An aperture is positioned along the path of the beam and an optical steering means is provided which can move the beam across the surface of the cornea. A first focusing means focuses the beam at the aperture, a second focusing means focuses the beam at desired points on the path of the beam, and a third focusing means confocally focuses specularly reflected light from the eye at the aperture.

Identification of a tissue boundary or interface is made by varying the focus of the system on the eye until a specular reflection is obtained from the interface of media or materials having different indices of refraction. Using signals generated by such reflections, the imaging system of the present invention identifies the boundary of tissue masses and uses this information to establish a datum from which subsequent ophthalmic operations with surgical lasers can be performed.

As implied above, the imaging system of the present invention may be operatively employed in conjunction with a surgical laser beam. With this combination, the light beam of the imaging system and the surgical laser beam are coaxially aligned and coincidentally focused by the focusing means. Thus, the light beam can be used both to identify a tissue interface and to visually monitor movement of the cutting laser.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
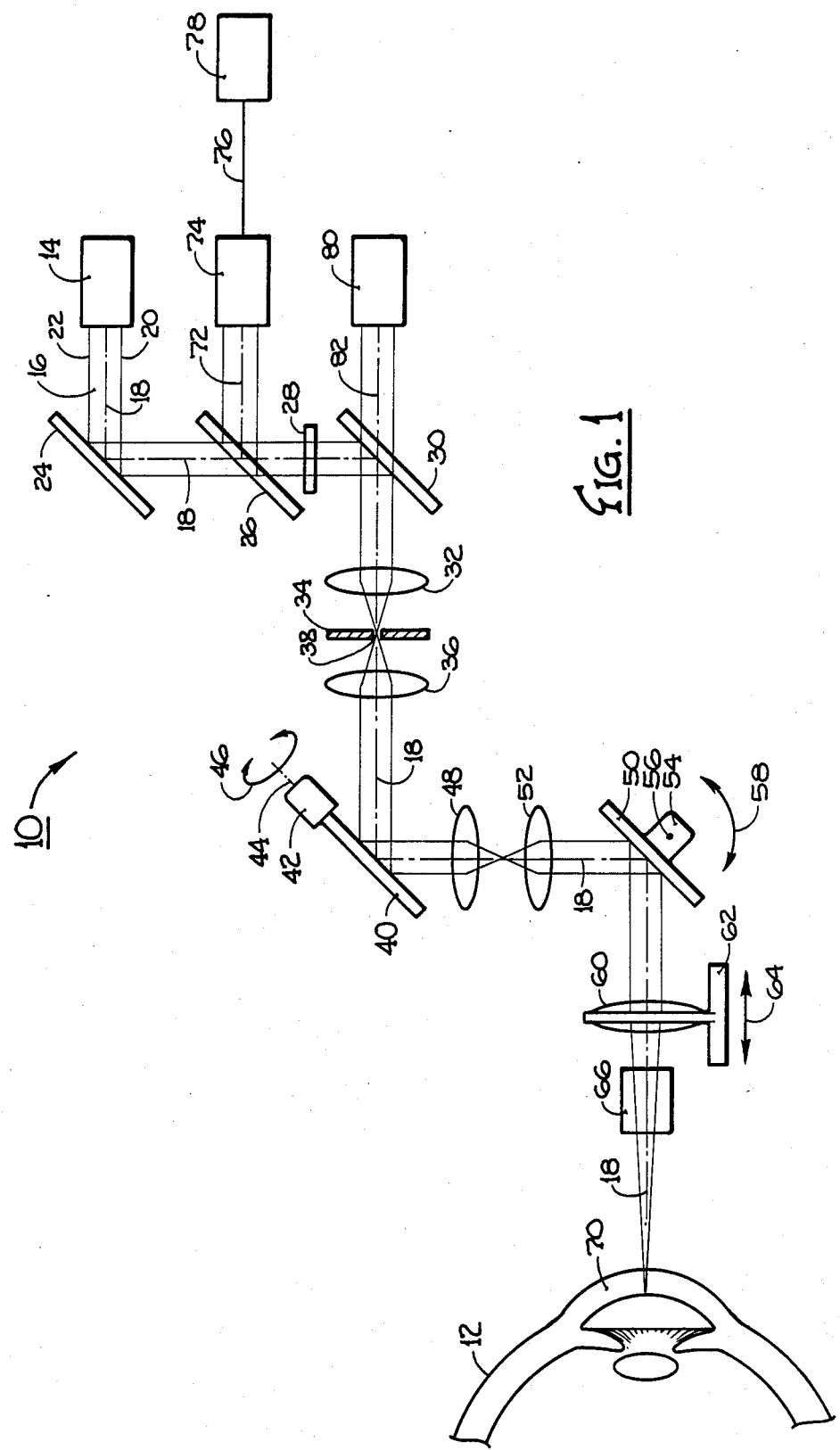
FIG. 1 is a schematic diagram of the optical elements of the present invention shown in operative relationship with a cross-sectional view of an eye.

In FIG. 1, an imaging system, generally designated 10, is shown in its operational relationship with an eye 12. As shown, imaging system 10 includes a light source 14 which radiates a beam 16 along an optical axis 18. For illustrative purposes, beam 16 is contained within an envelope defined by boundaries 20 and 22. Although several active media can be used within the contemplation and spirit of the present invention to produce beam 16, light source 14 is preferably a HeNe laser which emits light having a wavelength of approximately 632 nanometers.

After leaving light source 14, beam 16 is incident on turning mirror 24 and is reflected therefrom toward fifty percent (50%) mirror 26. At this point, beam 16 passes through 50% mirror 26 and continues along optical axis 18 to pass through filter 28 before being reflected by selectively reflective mirror 30 toward a spatial filter (unnumbered). For purposes of the present invention, the filter 28 is transparent to light from light source 14 and selectively reflective mirror 30 is completely reflective of light from light source 14.

From mirror 30, beam 16 is directed through the spatial filter which comprises, in order along optical axis 18, a convex lens 32, an aperture 34 and a convex lens 36. As is well known to the skilled artisan, such a combination focuses beam 16 at the pin hole 38 of aperture 34 for the purpose of limiting the quantity of light which is to be passed along optical axis 18. More specifically, convex lens 32 focuses beam 16 onto pin hole 38 of aperture 34. Further, as a confocal arrangement, convex lens 36 will focus light reflected along optical axis 18 onto pin hole 38 of aperture 34. Preferably, for the purposes of imaging system 10, pin hole 38 is approximately ten microns in diameter so that the focal depth of imaging system 10 will be approximately 5-10 microns.

The steerability of beam 16 within the imaging system 10 is provided by the concerted operation of galvanometric mirrors 40 and 50. This operation is disclosed in detail in our copending application Ser. No. 151,569 for an invention entitled "3-Dimensional Laser Beam Guidance System" which was filed on Feb. 2, 1988 and which is incorporated herein by reference. Further to this, however, it will be seen in FIG. 1 that a galvanometer 42 is operatively connected with galvanometric mirror 40 for rotating mirror 40 around the axis 44 in the directions of arrow 46. As will be appreciated by the skilled artisan, this movement of mirror 40 directs optical axis 18 of beam 16 from mirror 40 on paths which lie in a plane that is perpendicular to the plane of FIG. 1. From mirror 40, beam 16 passes through convex lenses 48 and 52 before being incident on galvanometric mirror 50. Clearly, the operation of mirror 50 is similar to that for mirror 40. Specifically, however, galvanometric mirror 50 is rotated by galvanometer 54 about the axis 56 in the directions of arrow 58 to steer beam 16 onto paths which radiate from mirror 50 in the plane of FIG. 1. From the above, and the referenced co-pending application, it will be understood that the beam 16 can be effectively steered in an x-y plane by either preprogrammed or manual movement of mirrors 40 and 50.

A focusing lens 60 is provided on optical axis 18 for the purpose of focusing beam 16 at a desired point on optical axis 18 that is coincident with a selectable point in the target area. Specifically, lens 60 is operatively connected with a focusing element 62 which will move lens 60 in the directions indicated by arrow 64 to focus beam 16. This arrangement is well known in the art and any focusing element 62 can be effectively used for the intended purposes. It is to be noted that, as mentioned above, imaging system 10 provides a confocal arrangement with both convex lens 32 and convex lens 36 focusing light onto pin hole 38 of aperture 34. It will be understood that this confocal arrangement is compatible with the operation of focusing lens 60. Importantly, beam 16 must be focusable at both pin hole 38 in aperture 34 and at a selectable point in the target area.

Various optical elements 66 can be incorporated into imaging system 10. For example, element 66 will preferably include components disclosed in our co-pending applications for an invention entitled "3-Dimensional Laser Beam Guidance System," which is cited above, and another application Ser. No. 154,859 for an invention entitled "Eyetracker and Method of Use" which was filed on the same date as this application and which is incorporated herein by reference. It is to be understood, however, that the imaging system 10 of the present invention is useable with any surgical laser system in which enhanced controllability is a prerequisite.

After being incident on eye 12, portions of beam 16 will be reflected back through system 10 along axis 18. Part of this reflected light will pass through pin hole 38 of aperture 34 and then be reflected by selectively reflective mirror 30 through filter 28. 50% mirror 26 will direct part of the reflected light along path 72 toward photomultiplier tube 74 where a signal proportional to the intensity of the light reflected from eye 12 is generated. This signal is then transmitted by electrical connection 76 to microprocessor 78 where the signal is used in accordance with a predetermined program for the operation of the imaging system 10.

It is to be appreciated that imaging system 10 is intended to be used with a surgical laser system. Thus, a cutting laser source 80 may be used and incorporated generally as shown in FIG. 1. Preferably, a laser source such as the one disclosed in our co-pending application entitled "Multiwavlength Laser Source" is incorporated. Regardless what source 80 may actually be, the generated cuttng laser beam 82 is to be coaxially aligned with beam 16 in imaging system 10 and confocally focused therewith. More precisely, cutting laser beam 82 and beam 16 can be placed in coaxial alignment and both steered and confocally focused while in such alignment by imaging system 10. It will be appreciated, however, that filter 28 blocks light from cutting laser source 80 to protect light source 14 and photomultiplier 74 from adverse effects which may be caused by cutting laser beam 82.

OPERATION

Figure 2:
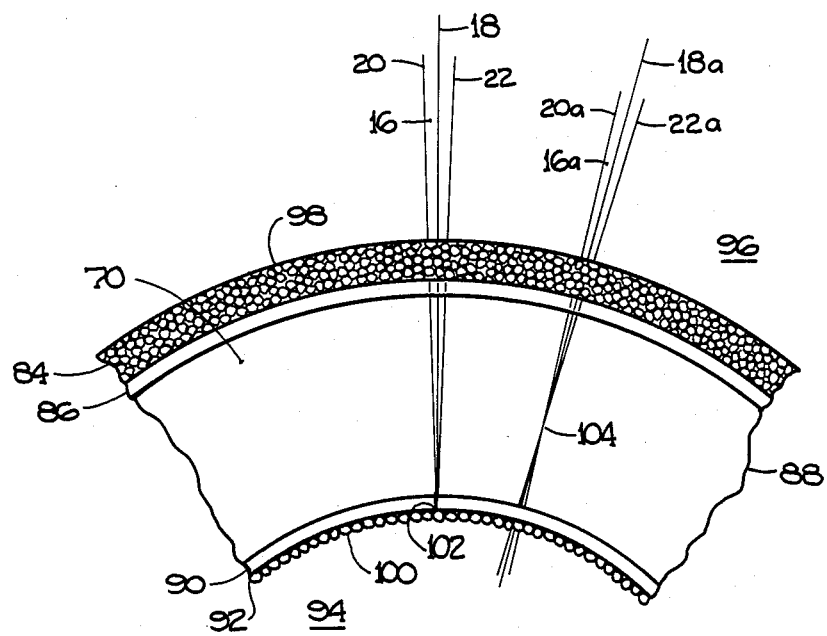
FIG. 2 is a detailed cross-section of the cornea of the eye as seen in FIG. 1.
Figure 3:
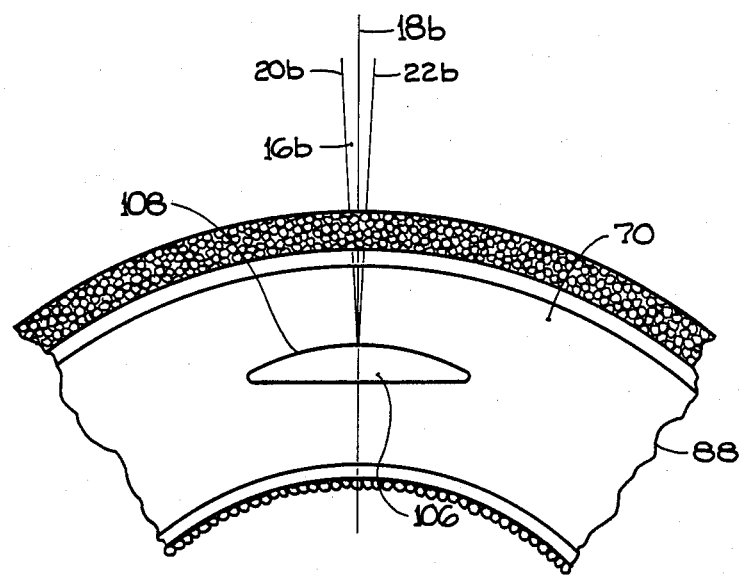
FIG. 3 is a detailed cross-section of the cornea as seen in FIG. 2 with an internal ablation.

Although the actual layout of components for the imaging system 10 is best seen in FIG. 1, its operation is best understood by reference to FIGS. 2 and 3. More specifically, the operation of imaging system 10 is understood by recognizing the way in which it causes a beam 16 to interact with eye 12.

In FIG. 2, a cross-section of cornea 70 is shown with its various layers identified. Specifically, cornea 70 comprises epithelium 84, Bowman's membrane 86, stroma 88, Descemet's membrane 90 and endothelium 92. Together, these layers form the cornea 70 which separates the aqueous humor 94 inside eye 12 behind cornea 70 from the air 96 which is outside eye 12 and in front of corea 70. For purposes of the present invention, the refractive index of air will be taken as 1.00. For all practical purposes, the refractive index of each layer in cornea 70 is the same as the refractive index of every other layer. The value of this refractive index is approximately 1.376. Importantly, the refractive index of aqueous humor 94 is approximately 1.336. Thus, there are discernable differences between the refractive index of air 96 and that of cornea 70, and between the refractive index of cornea 70 and that of aqueous humor 94.

Still referring to FIG. 2, it can be appreciated that as beam 16 passes from air 96 with refractive index 1 into cornea 70 with a refractive index of 1.376, part of beam 16 will be reflected at the interface 98 therebetween. The actual amount of light which is reflected will depend, of course, on the brilliance (i.e. concentration of photons) of beam 16 as it is incident on interface 98. Thus, if beam 16 is focused on interface 98, its brilliance is increased and the amount of reflected light is also increased. The same is true for beam 16 as it is incident on interface 100 between cornea 70, with refractive index 1.376, and aqueous humor 94, with refractive index 1.336. It happens, however, due to the magnitude of the differences between the respective refractive indices, focused light will be reflected form interface 98 with approximately one hundred (100) times the brilliance of that for focused light reflected from interface 100. Nevertheless, when beam 16 is focused at point 102 on interface 100, its brilliance in specular reflection significantly surpasses the brilliance of unfocused light reflected from interface 98. Further, as reflected light from interface 100 is radiated back through imaging system 10 along axis 18, the effect is enhanced by aperture 34 which effectively suppresses the unfocused light reflected from interface 98. On the other hand, because imaging system 10 is a confocal system, beam 16 is focused at both point 102 on interface 100 and at pinhole 38 of aperture 34. The result is that specularly reflected light from point 102 is passed through aperture 34, without loss of intensity, and is transmitted to photomultiplier 74 and microprocessor 78 for further processing in accordance with selected procedures.

This same explanation applies whenever beam 16 is focused at any other interface between media having different indices of refraction. Thus, interface 98 could likewise be imaged if beam 16 were focused thereon. On the other hand, whenever beam 16 is focused at a point, such as point 104 where there is no change in refractive index, there will be no specular reflection. In such cases, imaging system 10 generates no operational signal at photomultiplier 74. Interfaces 98 and 100, however, will generate operational signals and can thereby be indentified. In accordance with the operation of system 10, this is done merely by steering beam 16 with the concerted operation of mirrors 40 and 50 while simultaneously varying the focal point of beam 16 along optical axis 18 by operation of focusing element 62.

FIG. 3 presents a special situation of interest for the imaging system 10 of the present invention. Specifically, FIG. 3 shows an internal ablation 106 formed into stroma 88 of cornea 70. As will be appreciated by the skilled artisan, creation of internal ablation 106 creates interface 108 which will be detectable by imaging system 10 in the manner previously described. Thus, in accordance with the imaging system 10 of the present invention, beam 16 can be used to identify interfaces 98, 100 or 108 according to the desires and needs of the operator. Thereafter, cutting laser beam 82 can be selectively activated to cut at desired focal points relative to the established interface. Further, beam 16 and cutting laser beam 82 can be operated concurrently.

While the particular imaging system as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. An ocular imaging system for determining the location of an interface between media having different indices of refraction which comprises:
    a light source for radiating a beam;
    a pin hole aperture positioned along said beam;
    means for focusing said beam confocally with said aperture; and
    monitoring means responsive to the intensity of light that is specularly reflected through said aperture to indicate when said beam is focused on said interface.

2. An ocular imaging system as cited in claim 1 further comprising a steering means for moving said beam across said interface.

3. An ocular imaging system as cited in claim 2 wherein said aperture has a diameter of approximately ten microns.

4. An ocular imaging system as cited in claim 3 wherein said light source is a HeNe laser emitting light of approximately 632 nanometer wavelength.

5. An ocular imaging system as cited in claim 1 further comprising means to establish an intensity threshold above which threshold said monitoring means indicates said beam is focused on said interface.

6. An ocular imaging system as cited in claim 1 further comprising a source for a cutting laser, said cutting laser coaxially aligned with said beam for coincident focus.

7. An ocular imaging system as cited in claim 6 wherein said source for said cutting laser is a YSGG:Cr:Nd:Er crystal.

8. An ocular system for specularly imaging an interface between materials having different refractive indices which comprises:
    a light source for directing a beam of light along a path toward said interface;
    a pinhole aperture positioned in said path; means positioned in said path for steering said beam;
    means to adjustably focus said beam along said path; and
    monitoring means responsive to specular reflections from said interface through said aperture to indicate when said beam is focused on said interface.

9. A system as cited in claim 8 wherein said focusing means confocally focuses said beam with said aperture.

10. A system as cited in claim 9 wherein said aperture has a diameter of approximately ten microns.

11. A system as cited in claim 10 wherein said light source is a HeNe laser emitting light of approximately 632 nanometer wavelength.

12. A system as cited in claim 11 further comprising means to establish an intensity threshold above which threshold said monitoring means indicates said beam is focused on said interface.

13. A system as cited in claim 8 further comprising a source for a cutting laser, said cutting laser coaxially aligned with said beam for coincident focus.

14. A system as cited in claim 13 wherein said source for said cutting laser is a YSGG:Cr:Nd:Er crystal.

15. A method for imaging the interface between tissues having different indices of refraction which comprises the steps of:
(A) Aiming a beam of light toward said interface;
(B) Positioning an aperture along said beam;
(C) Focusing said beam through said aperture and onto said interface for obtaining specular reflections from said interface;
(D) Confocally focusing said reflections through said aperture; and
(E) Determining when said confocal focusing is accomplished.

16. A method as cited in claim 15 further comprising the step of:
coaxially aligning a cutting laser for coincidental focusing with said beam.

17. A method as cited in claim 16 wherein said determining step comprises monitoring the intensity of said reflections to indicate confocal focusing when said intensity surpasses a predetermined threshold.

* * * * *